(12) United States Patent
Sun et al.

(10) Patent No.: US 12,183,479 B2
(45) Date of Patent: Dec. 31, 2024

(54) CHEMICAL FOAMING AGENTS CONTAINING TOSYL GROUPS

(71) Applicant: Dow Global Technologies LLC, Midland, MI (US)

(72) Inventors: Gangwei Sun, Shanghai (CN); Hongyu Chen, Shanghai (CN); Mohamed Esseghir, Lawrenceville, NJ (US); Renhua Fan, Shanghai (CN); Shuo-En Wang, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 917 days.

(21) Appl. No.: 17/252,590

(22) PCT Filed: Jun. 15, 2018

(86) PCT No.: PCT/CN2018/091433
§ 371 (c)(1),
(2) Date: Dec. 15, 2020

(87) PCT Pub. No.: WO2019/237318
PCT Pub. Date: Dec. 19, 2019

(65) Prior Publication Data
US 2021/0265077 A1  Aug. 26, 2021

(51) Int. Cl.
| | | |
|---|---|---|
| *H01B 3/44* | (2006.01) |
| *C07C 311/49* | (2006.01) |
| *C07C 311/62* | (2006.01) |
| *C07D 251/66* | (2006.01) |
| *C07D 257/04* | (2006.01) |
| *C08J 9/10* | (2006.01) |

(52) U.S. Cl.
CPC .......... *H01B 3/441* (2013.01); *C07C 311/49* (2013.01); *C07C 311/62* (2013.01); *C07D 251/66* (2013.01); *C07D 257/04* (2013.01); *C08J 9/105* (2013.01); *C08J 2203/04* (2013.01); *C08J 2323/04* (2013.01)

(58) Field of Classification Search
CPC ................. C07C 311/49; C07C 311/58; C07C 311/62; C07D 251/66; C07D 257/04; C08J 9/102; C08J 9/105; C08J 2203/04; C08J 2323/04; C08J 2323/06; C08J 2423/06; H01B 3/44; H01B 3/441
See application file for complete search history.

(56) References Cited

U.S. PATENT DOCUMENTS

| | | |
|---|---|---|
| 3,374,190 A | 3/1968 | Herweh et al. |
| 4,209,632 A | 6/1980 | Hunter |
| 5,032,621 A | 7/1991 | Buckmaster et al. |
| 5,246,783 A | 9/1993 | Spenadel et al. |
| 6,064,008 A | 5/2000 | Craton |
| 6,496,629 B2 | 12/2002 | Ma et al. |
| 6,714,707 B2 | 3/2004 | Rossi et al. |
| 6,864,298 B2 | 3/2005 | Maletzko et al. |
| 7,767,725 B2 | 8/2010 | Brix et al. |
| 10,160,844 B2 | 12/2018 | Lee |
| 2005/0112356 A1 | 5/2005 | Rynd et al. |
| 2006/0045439 A1 | 3/2006 | Brown et al. |
| 2009/0018225 A1 | 1/2009 | Gemmel et al. |
| 2010/0252947 A1 | 10/2010 | Brix et al. |
| 2011/0021651 A1 | 1/2011 | Mayeres et al. |
| 2013/0090398 A1 | 4/2013 | Glew et al. |
| 2014/0080933 A1 | 3/2014 | Abe et al. |
| 2017/0190862 A1 | 7/2017 | Ahn et al. |
| 2017/0306123 A1* | 10/2017 | Uno ........................ C08L 23/12 |
| 2017/0342230 A1* | 11/2017 | Bordeanu ............. C07C 271/12 |

FOREIGN PATENT DOCUMENTS

| | | |
|---|---|---|
| CA | 1096878 | 3/1981 |
| CA | 2523861 C | 2/2011 |
| CN | 101959944 | 1/2011 |
| CN | 103483227 | 1/2014 |
| CN | 104892464 | 9/2015 |
| CN | 105440445 | 3/2016 |
| JP | 2004161692 | 6/2004 |
| JP | 2006339099 | 12/2006 |
| JP | 2016160416 A | 9/2016 |
| RU | 2311430 C2 | 11/2007 |
| WO | 2014099335 | 6/2014 |
| WO | 2014099335 A2 | 6/2014 |
| WO | 2015162242 | 10/2015 |
| WO | 2016092274 | 6/2016 |
| WO | 2017166004 | 10/2017 |

OTHER PUBLICATIONS

Cremlyn, "Sulphonohydrazides and Related Compounds. Part XII. Some Arylsulphonyl Derivatives of Carbonohydrazids and Related Hydrazides", J. Chem. Soc. (C). Org., 1970, p. 2629-2631, vol. 19.
Herweh, "The synthesis and characterization of some 2,4,6-triaryl and alkylsulfonylhydrazido-s-triazines", J. Heterocyclic Chem., 1966, p. 70-73, vol. 3.
Office Action from corresponding Russian Patent Application No. 2020142794 dated Oct. 8, 2021.
Search report from corresponding European Application No. 18922586. 5, dated Dec. 9, 2021.
Examination Report from corresponding Indian Patent Application No. 202017054628 dated Jun. 21, 2022.
Bose, "Performance of a novel activator for azodicarbonamide for sponge and cellular rubber," Rubber World, 1993, p. 1-6.
Zhang, Scale-Up of Extrusion Foaming Process for Manufacture of Polystyrene Foams Using Carbon Dioxide, Master's Thesis, University of Toronto, 2010.
Office Action Report Letter from corresponding Korean Patent Application No. 2020-7037297 dated Feb. 10, 2023.
Office Action Report Letter from corresponding Chinese Application No. 201880094490.2 dated Jul. 15, 2022.

\* cited by examiner

*Primary Examiner* — John M Cooney (57) ABSTRACT

Chemical foaming agents having p-toluenesulfonyl groups. Processes for preparing foamed polyolefin compositions using chemical foaming agents having p-toluenesulfonyl groups. Articles of manufacture containing formed polyolefins prepared using chemical foaming agents having p-toluenesulfonyl groups.

4 Claims, 3 Drawing Sheets

CHEMICAL FOAMING AGENTS CONTAINING TOSYL GROUPS

FIELD

Various embodiments relate to chemical foaming agents containing tosyl groups. Additional embodiments relate to employing tosyl-group-containing chemical foaming agents in foamable polyolefin compositions to form foamed polyolefins. Further embodiments relate to using such foamed polyolefins as an insulation layer in telecommunication cables, particularly high-frequency coaxial cables.

INTRODUCTION

Typically, the insulation layer of a high-frequency telecommunication cable is produced from a mixture of a polyolefin and a nucleating agent (e.g., a chemical foaming agent), where the mixture is foamed using a gas-injection extrusion process. In the foaming process, a blowing agent, such as nitrogen or carbon dioxide, is injected under pressure directly into the polyolefin melt mixture so as to dissolve within the melt and to form a homogenous mixture with the melt. This homogeneous mixture is kept under pressure (the amount of which is determined by the gas used and the melt pressure), and this pressure is maintained throughout to the extruder in order to prevent the gas from expanding the melt prematurely. On exiting the die, the melt pressure decreases to atmospheric pressure and the dissolved gas expands immediately in the melt to form the foam insulation coated on a conductor, e.g., copper wire.

Insulation having a higher expansion ratio, a finer cell size, and a more uniform cell distribution is desirable to meet the high transmission efficiency in telecom cable. Adding a nucleating agent, such as a chemical foaming agent, is an effective technique used to reduce the cell size, enhances the cell population and promote a uniform cell distribution. Azodicarbonamide ("ADCA") and 4,4'-oxybis-benzenesulfonylhydrazide ("OBSH"), which can thermally decompose in an extruder and form a number of fine nuclei in the polymer melt, have been used as nucleating agents for telecom cable insulation. However, the decomposition byproducts of ADCA and OBSH are polar which can negatively affect the electrical performance the foamed polymer. Accordingly, improvements in chemical foaming agents are desired.

SUMMARY

One embodiment is a chemical foaming agent comprising one or more of the following compounds shown as structures (I) through (IX):

structure (I)

structure (II)

structure (III)

structure (IV)

structure (V)

structure (VI)

structure (VII)

structure (VIII)

structure (IX)

where Ts is a p-toluenesulfonyl group.

Another embodiment is a process of foaming a polyolefin, the process comprising:
(a) combining a polyolefin with a chemical foaming agent to thereby form a foamable polyolefin composition; and
(b) subjecting the foamable polyolefin composition to a foaming process,
wherein the chemical foaming agent comprises one or more of the following compounds shown as structures (I) through (IX):

structure (I)

where Ts is a p-toluenesulfonyl group.

BRIEF DESCRIPTION OF THE DRAWINGS

Reference is made to the accompanying drawings in which.

DETAILED DESCRIPTION

Figure 1:
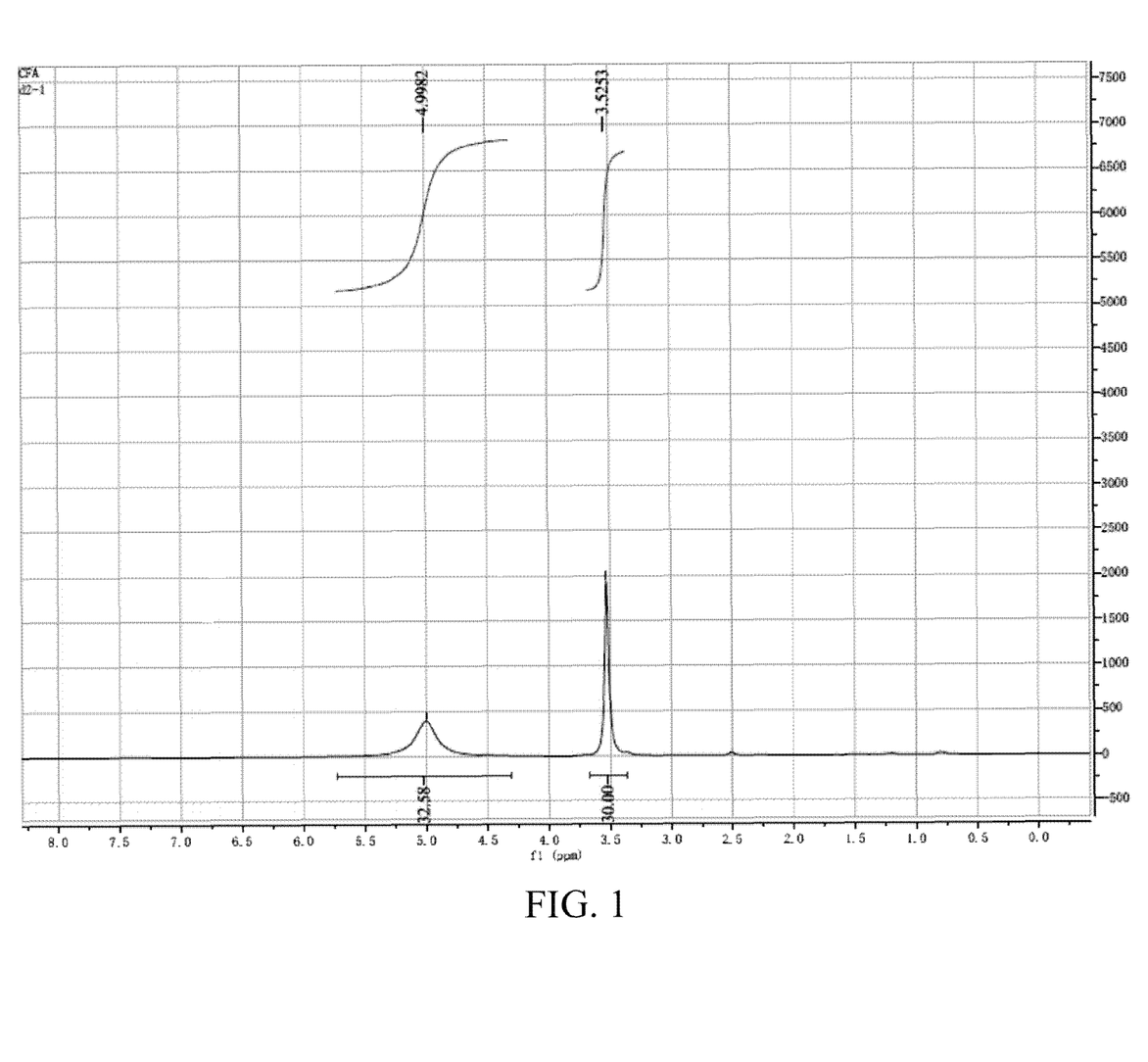
FIG. 1 is a proton NMR spectrum of a tosyl-group-containing chemical foaming agent according to one aspect of the present disclosure.
Figure 2:
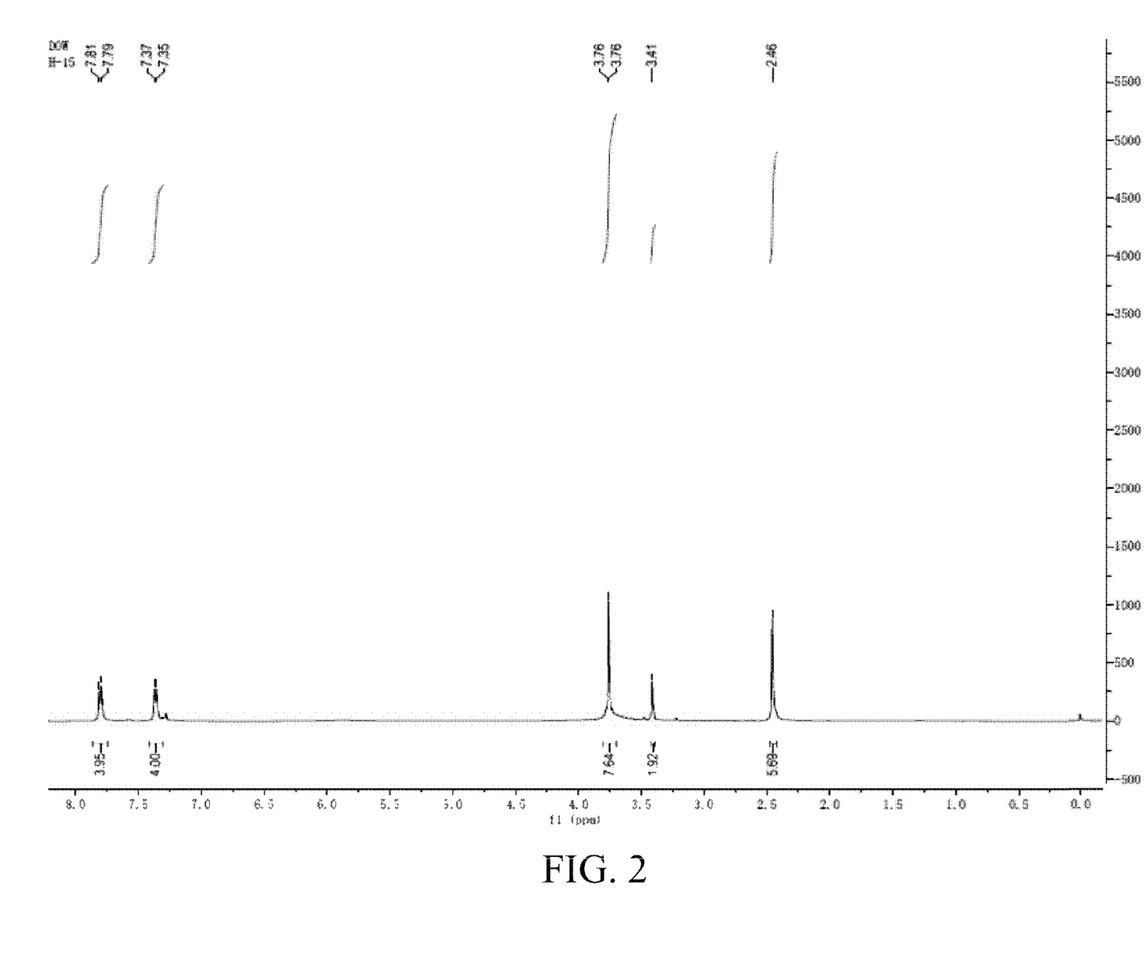
FIG. 2 is a proton NMR spectrum of a tosyl-group-containing chemical foaming agent according to another aspect of the present disclosure.
Figure 3:
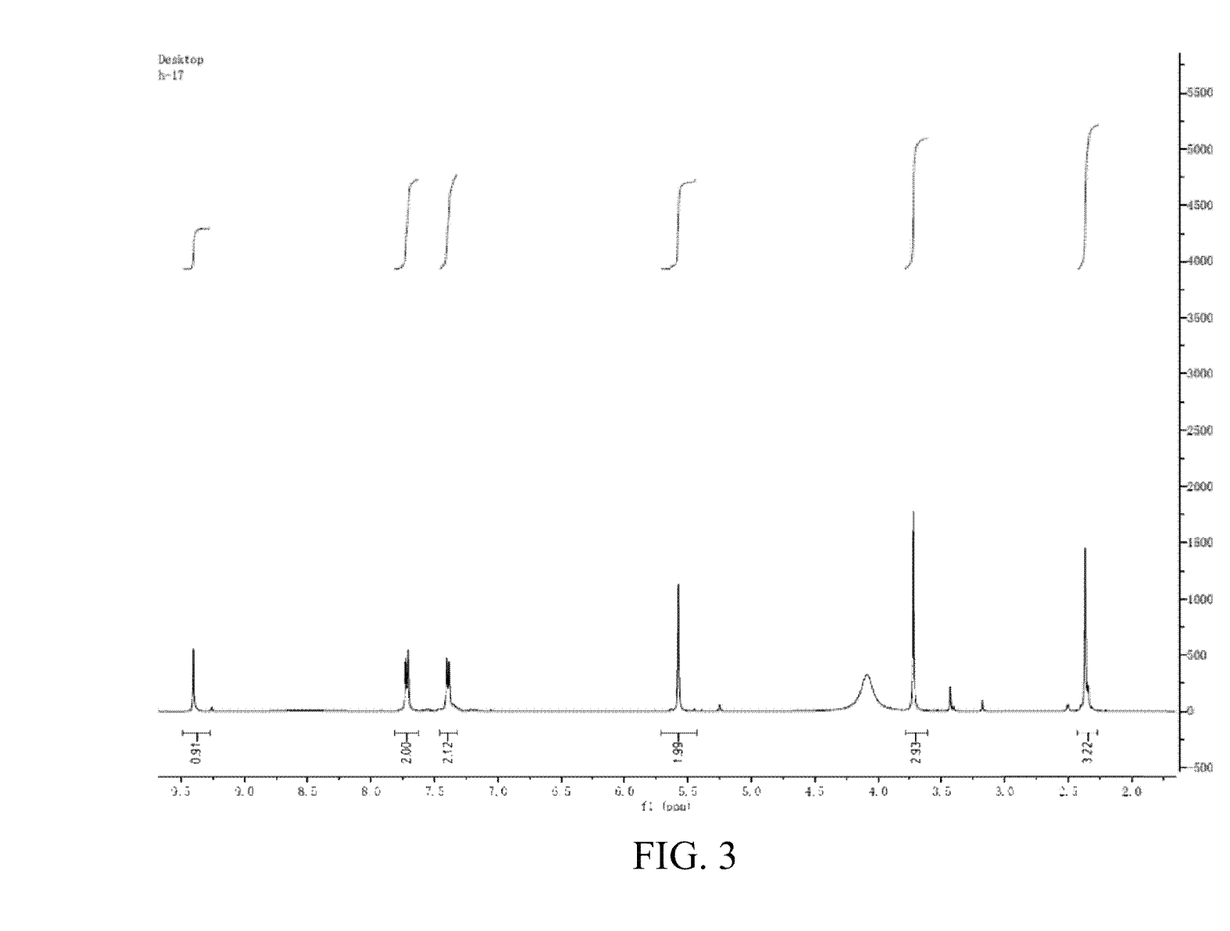
FIG. 3 is a proton NMR spectrum of a tosyl-group-containing chemical foaming agent according to yet another aspect of the present disclosure.

Various embodiments of the present disclosure concern chemical foaming agents containing tosyl groups. Further embodiments of the present invention concern a foamable polyolefin composition comprising a polyolefin and a chemical foaming agent. Further embodiments concern a process for foaming a foamable polyolefin composition and the resulting foamed polyolefin composition. Additionally, various embodiments concern articles of manufacture prepared from such foamed polyolefin compositions, such as insulation layers in telecommunication cables.

Chemical Foaming Agent

As just noted, various embodiments of the present disclosure relate to chemical foaming agents containing tosyl groups. As used herein, the term "chemical foaming agent" denotes a compound or combination of compounds that liberate gases as a result of chemical reactions, such as decomposition at temperatures above a certain threshold. As known to those skilled in the art, the term "tosyl" denotes a p-toluenesulfonyl functional group, which has the following structure:

When shown in chemical foaming agent structures herein, a tosyl group may be denoted by the abbreviation "Ts."

Suitable tosyl-group-containing chemical foaming agents can have a decomposition temperature of less than 200° C., less than 190° C., less than 180° C., less than 170° C., or less than 160° C. Additionally, suitable tosyl-group-containing chemical foaming agents can have a decomposition temperature of at least 90° C., at least 100° C., or at least 110° C.

Upon decomposition, liberated gases from suitable tosyl-group-containing chemical foaming agents can be primarily composed of nitrogen ($N_2$), carbon monoxide (CO), or a combination of both nitrogen and carbon monoxide. As used herein, "primarily" means greater than 50% by volume ("vol %"). In one or more embodiments, gases liberated from suitable tosyl-group-containing chemical foaming agents upon decomposition can be composed of at least 60 vol %, at least 70 vol %, at least 80 vol %, at least 90 vol %, or at least 99 vol % nitrogen, carbon monoxide, or a combination of both nitrogen and carbon monoxide. In further embodiments, gases liberated from suitable tosyl-group-containing chemical foaming agents upon decomposition can contain less than 50 vol % water, less than 40 vol % water, less than 30 vol % water, less than 20 vol % water, less than 10 vol % water, or less than 1 vol % water. In still further embodiments, gases liberated from suitable tosyl-group-containing chemical foaming agents upon decomposition can contain less than 50 vol %, less than 40 vol %, less than 30 vol %, less than 20 vol %, less than 10 vol %, or less than 1 vol % of combined polar compounds. As used herein, the term "polar" denotes a molecule having a net dipole as the result of opposing charges (i.e., having partial positive and partial negative charges) from polar bonds arranged asymmetrically. Polar bonds are bonds between carbon atoms and other atoms having relatively high electronegativity, such as O, N, F, and Cl.

In one or more embodiments, suitable tosyl-group-containing chemical foaming agents can have a gas yield upon decomposition of at least 100 milliliters of gas per gram of foaming agent ("ml/g"), at least 110 ml/g, at least 120 ml/g, at least 130 ml/g, at least 140 ml/g, at least 150 ml/g, at least 160 ml/g, at least 170 ml/g, at least 180 ml/g, at least 190 ml/g, or at least 200 ml/g. Additionally, suitable tosyl-group-containing chemical foaming agents can have a gas yield upon decomposition of up to 300 ml/g, up to 275 ml/g, or up to 225 ml/g.

In various embodiments, suitable tosyl-group-containing chemical foaming agents can have a weight loss upon decomposition of at least 50 percent by weight ("wt %"), at least 55 wt %, at least 60 wt %, at least 65 wt %, at least 70 wt %, at least 75 wt %, or at least 80 wt %. Additionally, suitable tosyl-group-containing chemical foaming agents can have a weight loss upon decomposition of up to 90 wt %, or up to 85 wt %.

The tosyl-group-containing chemical foaming agents useful herein can comprise one or more of the following compounds shown in structures (I) through (IX):

structure (VIII)

structure (IX)

In one or more embodiments, the chemical foaming agent can comprise one or more of the compounds shown in structures (I) through (III), above. In other embodiments, the chemical foaming agent can consist of one or more of the compounds shown in structures (I) through (III), above.

The tosyl-group-containing chemical foaming agent can be prepared by any known or hereafter discovered methods in the art. Detailed synthesis procedures for preparing the tosyl-group-containing compounds of structures (I) through (III) are provided in the Examples section, below.

Polyolefin

As noted above, aspects of the present disclosure relate to foamable polyolefin compositions, which comprise a polyolefin. "Polyolefin" means a polymer derived from one or more simple olefin monomers, e.g., ethylene, propylene, 1-butene, 1-hexene, 1-octene and the like. The olefin monomers can be substituted or unsubstituted and if substituted, the substituents can vary widely. If the polyolefin is to contain unsaturation, then the polyolefin can contain one or more nonconjugated-diene comonomers, such as 1,7-octadiene, 1,9-decadiene, 1,11-dodecadiene, 1,13-tetradecadiene, 7-methyl-1,6-octadiene, 9-methyl-1,8-decadiene and the like. Many polyolefins are thermoplastic. Polyolefins include, but are not limited to, polyethylene, polypropylene, polybutene, polyisoprene, and their various interpolymers.

In one or more embodiments, the polyolefin can comprise an ethylene-based polymer. As used herein, "ethylene-based" polymers are polymers prepared from ethylene monomers as the primary (i.e., greater than 50 weight percent ("wt %")) monomer component, though other comonomers may also be employed. "Polymer" means a macromolecular compound prepared by reacting (i.e., polymerizing) monomers of the same or different type, and includes homopolymers and interpolymers. "Interpolymer" means a polymer prepared by the polymerization of at least two different monomer types. This generic term includes copolymers (usually employed to refer to polymers prepared from two different monomer types), and polymers prepared from more than two different monomer types (e.g., terpolymers (three different monomer types) and quaterpolymers (four different monomer types)).

In various embodiments, the ethylene-based polymer can be an ethylene homopolymer. As used herein, "homopolymer" denotes a polymer comprising repeating units derived from a single monomer type, but does not exclude residual amounts of other components used in preparing the homopolymer, such as chain transfer agents.

In one or more embodiments, the ethylene-based polymer can be an ethylene/alpha-olefin ("α olefin") interpolymer having an α-olefin content of at least 1 wt %, at least 5 wt %, at least 10 wt %, at least 15 wt %, at least 20 wt %, or at least 25 wt % based on the entire interpolymer weight. These interpolymers can have an α-olefin content of less than 50 wt %, less than 45 wt %, less than 40 wt %, or less than 35 wt % based on the entire interpolymer weight. When an α-olefin is employed, the α-olefin can be a C3-20 (i.e., having 3 to 20 carbon atoms) linear, branched or cyclic α-olefin. Examples of C3-20 α-olefins include propene, 1 butene, 4-methyl-1-pentene, 1-hexene, 1-octene, 1-decene, 1 dodecene, 1 tetradecene, 1 hexadecene, and 1-octadecene. The α-olefins can also have a cyclic structure such as cyclohexane or cyclopentane, resulting in an α-olefin such as 3 cyclohexyl-1-propene (allyl cyclohexane) and vinyl cyclohexane. Illustrative ethylene/α-olefin interpolymers include ethylene/propylene, ethylene/1-butene, ethylene/1-hexene, ethylene/1-octene, ethylene/propylene/1-octene, ethylene/propylene/1-butene, and ethylene/1-butene/1-octene.

In various embodiments, the ethylene-based polymer can be a low-density polyethylene ("LDPE"). LDPEs are generally highly branched ethylene homopolymers, and can be prepared via high pressure processes (i.e., HP-LDPE). LDPEs suitable for use herein can have a density ranging from 0.91 to 0.94 g/cm3. In various embodiments, the ethylene-based polymer is a high-pressure LDPE having a density of at least 0.915 g/cm$^3$, but less than 0.94 g/cm$^3$, or less than 0.93 g/cm$^3$. Polymer densities provided herein are determined according to ASTM International ("ASTM") method D792. LDPEs suitable for use herein can have a melt index ($I_2$) of less than 20 g/10 min., or ranging from 0.1 to 10 g/10 min., from 0.5 to 5 g/10 min., from 1 to 3 g/10 min., or an $I_2$ of 2 g/10 min. Melt indices provided herein are determined according to ASTM method D1238. Unless otherwise noted, melt indices are determined at 190° C. and 2.16 Kg (i.e., $I_2$). Generally, LDPEs have a broad molecular weight distribution ("MWD") resulting in a relatively high polydispersity index ("PDI;" ratio of weight-average molecular weight to number-average molecular weight).

In various embodiments, the ethylene-based polymer can be a linear-low-density polyethylene ("LLDPE"). LLDPEs are generally ethylene-based polymers having a heterogeneous distribution of comonomer (e.g., α-olefin monomer), and are characterized by short-chain branching. For example, LLDPEs can be copolymers of ethylene and α-olefin monomers, such as those described above. LLDPEs suitable for use herein can have a density ranging from 0.916 to 0.925 g/cm$^3$. LLDPEs suitable for use herein can have a melt index ($I_2$) ranging from 1 to 20 g/10 min., or from 3 to 8 g/10 min.

In various embodiments, the ethylene-based polymer can be a very-low-density polyethylene ("VLDPE"). VLDPEs may also be known in the art as ultra-low-density polyethylenes, or ULDPEs. VLDPEs are generally ethylene-based polymers having a heterogeneous distribution of comonomer (e.g., α-olefin monomer), and are characterized by short-chain branching. For example, VLDPEs can be copolymers of ethylene and α-olefin monomers, such as one or more of those α-olefin monomers described above. VLDPEs suitable for use herein can have a density ranging from 0.87 to 0.915 g/cm$^3$. VLDPEs suitable for use herein can have a melt index ($I_2$) ranging from 0.1 to 20 g/10 min., or from 0.3 to 5 g/10 min.

In various embodiments, the ethylene-based polymer can be a medium-density polyethylene ("MDPE"). MDPEs are ethylene-based polymers having densities generally ranging from 0.926 to 0.940 g/cm$^3$. In various embodiments, the MDPE can have a density ranging from 0.930 to 0.940 g/cm$^3$. The MDPE can have a melt index ($I_2$) ranging from 0.1 g/10 min, or 0.2 g/10 min, or 0.3 g/10 min, or 0.4 g/10 min, up to 5.0 g/10 min, or 4.0 g/10 min, or, 3.0 g/10 min or 2.0 g/10 min, or 1.0 g/10 min, as determined according to ASTM D-1238 (190° C./2.16 kg).

In various embodiments, the ethylene-based polymer can be a high-density polyethylene ("HDPE"). HDPEs are ethylene-based polymers having densities greater than 0.940 g/cm$^3$. In an embodiment, the HDPE has a density from 0.945 to 0.97 g/cm$^3$, as determined according to ASTM D-792. The HDPE can have a peak melting temperature of at least 130° C., or from 132 to 134° C. The HDPE can have a melt index ($I_2$) ranging from 0.1 g/10 min, or 0.2 g/10 min, or 0.3 g/10 min, or 0.4 g/10 min, up to 5.0 g/10 min, or 4.0 g/10 min, or, 3.0 g/10 min or 2.0 g/10 min, or 1.0 g/10 min, or 0.5 g/10 min, as determined according to ASTM D-1238 (190° C./2.16 kg). Also, the HDPE can have a PDI in the range of from 1.0 to 30.0, or in the range of from 2.0 to 15.0, as determined by gel permeation chromatography.

In various embodiments, the ethylene-based polymer can be used alone or in combination with one or more other types of ethylene-based polymers (e.g., a blend of two or more ethylene-based polymers that differ from one another by monomer composition and content, catalytic method of preparation, etc).

Production processes used for preparing ethylene-based polymers are wide, varied, and known in the art. Any conventional or hereafter discovered production process for producing ethylene-based polymers having the properties described above may be employed for preparing the ethylene-based polymers described herein. In general, polymerization can be accomplished at conditions known in the art for Ziegler-Natta or Kaminsky-Sinn type polymerization reactions, that is, at temperatures from 0 to 250° C., or 30 or 200° C., and pressures from atmospheric to 10,000 atmospheres (1,013 megaPascal ("MPa")). In most polymerization reactions, the molar ratio of catalyst to polymerizable compounds employed is from 10-12:1 to 10 1:1, or from 10-9:1 to 10-5:1.

In one or more embodiments, the polyolefin can comprise high-density polyethylene ("HDPE"), low-density polyethylene ("LDPE"), or blends thereof. In various embodiments, the polyolefin is a blend of HDPE and LDPE.

Nonlimiting examples of suitable, commercially available HDPEs include, but are not limited to, DOW High Density Polyethylene resins; CONTINUUM™, UNIVAL™, and AXELERON™ high-density polyethylene resins; ELITE™ 5960G; HDPE KT 10000 UE; HDPE KS 10100 UE; and HDPE 35057E, each available from The Dow Chemical Company Midland, Michigan, USA; SURPASS™ available from Nova Chemicals Corporation, Calgary, Alberta, Canada; BS2581 available from *Borealis*; Hostalen ACP 5831D available from Lyondell/Basell; RIGIDEX™ HD5502S available from INEOS Olefins & Polymers Europe; SABIC™ B5823 and SABIC™ B5421 available from Sabic; and HDPE 5802 and BM593 available from Total.

Commercially available LDPE resins include, but are not limited to, DOW Low Density Polyethylene resins available from The Dow Chemical Company, such as AXELERON™ LDPEs (e.g., AXELERON™ CX 1258 NT) and, in general, any fractional melt flow index ("MFI") resin for use in heavy duty bags or agricultural films, such as those available from *Borealis*, Basel, Sabic, and others.

Blends of two or more ethylene-based polymers (e.g., HDPE/LDPE blends) may be prepared by any suitable means known in the art, such as dry blending in a pelletized form in desired proportions followed by melt blending in a suitable apparatus, such as a screw extruder or a BANBURY™ mixer. Dry-blended pellets may be directly melt processed into a final solid state article by, for example, extrusion or injection molding. The blends may also be made by direct polymerization. Direct polymerization may use, for example, one or more catalysts in a single reactor or two or more reactors in series or parallel while varying at least one of operating conditions, monomer mixtures, and catalyst choice.

When an HDPE/LDPE blend is employed as the polyolefin, the amount of HDPE in the foamable polyolefin composition, based on the total weight of the composition, can be at least 45 wt %, at least 55 wt %, or at least 60 wt %. The amount of HDPE in the foamable polyolefin composition, based on the total weight of the composition, can be 95 wt % or less, 85 wt % or less, or 80 wt % or less. The amount of LDPE in the foamable polyolefin composition, based on the total weight of the composition, can be at least 4 wt %, at least 14 wt %, or at least 19 wt %. The amount of LDPE in the foamable polyolefin composition, based on the total weight of the composition, can be 54 wt % or less, 44 wt % or less, or 39 wt % or less. Additionally, the HDPE component of the blend can comprise two or more grades of HDPE, and the LDPE component of the blend can comprise two or more grades of LDPE. The HDPE/LDPE blend can have a melt index ($I_2$) ranging from 0.1 to 4 g/10 min., or from 0.15 to 4 g/10 min.

Foamable Polyolefin Composition

As noted above, the chemical foaming agent and polyolefin can be combined to form a foamable polyolefin composition. In various embodiments, the chemical foaming agent can be present in the foamable polyolefin composition in an amount ranging from 0.01 to 1 wt %, from 0.05 to 0.6 wt %, from 0.1 to 0.4 wt %, from 0.1 to 0.2 wt %, or from 0.14 to 0.16 wt %, based on the total weight of the foamable polyolefin composition.

The chemical foaming agent can be added to the foamable polyolefin composition by any conventional means. The chemical foaming agent can be added neat, in combination with one or more other additives, e.g., antioxidant, cell stabilizer, etc., or as part of a masterbatch. The chemical foaming agent can be mixed with the foamable polyolefin composition to achieve an essentially homogeneous dispersion of chemical foaming agent in the foamable polyolefin composition and to this end, batch mixing, e.g., through the use of a Banbury mixer, may be employed. Alternatively, the foamable polyolefin composition can be prepared in a continuous mixer such as through the use of a twin-screw extruder or a BUSS™ kneader. If the chemical foaming agent is first mixed with the foamable polyolefin composition in an extruder, then it is typically added to the foamable polyolefin composition prior to injection of blowing agent for foaming.

Additives

The foamable polyolefin composition may contain one or more additives as necessary or desired. Representative additives include but are not limited to, processing aids, lubricants, stabilizers (antioxidants), foaming aids, nucleating agents, surfactants, flow aids, viscosity control agents, coloring agents, copper inhibitors, and the like. These additives can be added to the polymer(s) either before or during processing. The amount of any particular additive in the polyolefin composition can be from 0.01 to 1 wt %, from 0.01 to 0.5 wt %, or from 0.01 to 0.3 wt %, and the total amount of additives in the polyolefin composition, if present at all, can be from 0.01 to 5 wt %, from 0.01 to 2 wt %, or from 0.01 to 1 wt %.

Physical Blowing Agent

In preparing a foamed polyolefin, a physical blowing agent may also be employed in addition to the above-described chemical foaming agent. The physical blowing agent is one or more agents suitable for the selected extrusion temperature, foaming conditions, foam-forming method, and the like. When an insulating foam layer in the final form is to be formed simultaneously with extrusion forming, an inert gas such as nitrogen, carbon gases (e.g., CO, $CO_2$, etc.), helium, argon and the like; hydrocarbon gases such as methane, propane, butane, pentane and the like; halogenated hydrocarbon gases such as dichlorodifluoromethane, dichloromonofluoromethane, monochlorodifluoromethane, trichloromonofluoromethane, monochloropentafluoroethane, trichlorotrifluoroethane and the like can be used. The amount of physical blowing agent to be used can vary. Typically, it can be 0.001 to 0.1 parts by weight, or 0.005 to 0.05 parts by weight, per 100 parts by weight of the polyolefin composition to be foamed. The physical blowing agent may be mixed in advance with the polyolefin to be foamed or may be supplied into an extruder from a supply opening formed on the barrel of the extruder.

Foaming Process

The foamable polyolefin composition described herein can be foamed using any conventional or hereafter-discovered methods and equipment. Typically, a foamed polyolefin is produced by extruding the foamable polyolefin composition containing a nucleator or chemical foaming agent using an extruder operated under foaming extrusion conditions, e.g., injection of a physical blowing agent while the composition is in a high-pressure zone and then extruding the composition to a low-pressure zone. Foaming processes are further described by C. P. Park in *Polyolefin Foam*, Chapter 9, *Handbook of Polymer Foams and Technology*, edited by D. Klempner and K. C. Frisch, Hanser Publishers (1991).

In one embodiment, a typical extrusion foaming process uses a physical blowing agent (e.g., $CO_2$) to produce a foamed cable insulation as described in CA 2 523 861 C, *Low Loss Foam Composition and Cable Having Low Loss Foam Layer*. Dissolution of the physical blowing agent into the polymer melt is governed by Henry's law as reported for example in the work of H. Zhang (below) and others. Solubility is a function of the saturation pressure and the Henry's law constant, which itself is a function of temperature. H. Zhang, *Scale-Up of Extrusion Foaming Process for Manufacture of Polystyrene Foams Using Carbon Dioxide*, Master's Thesis, University of Toronto, 2010 (https://tspace.library.utoronto.ca/bitstream/1807/25536/1/Zhang_Hongtao_201011_MASc_thesis.pdf). Also see *Foam Extrusion: Principles and Practice* by Shau-Tarng Lee, editor.

Foamed Composition

The resulting foamed polyolefin composition can have a foaming level ("porosity") of at least 70, at least 75, at least 77, or at least 78 percent, measured by comparing the densities of the neat polyolefin and the foamed polyolefin composition. In various embodiments, the foaming level of the foamed polyolefin composition can be less than 80 percent. In various embodiments, the foamed polyolefin composition can have an average cell size of less than 215 µm, less than 210 µm, or less than 207 µm. Additionally, the foamed polyolefin composition can have an average cell size of at least 180 µm, or at least 190 µm. In various embodiments, the foamed composition can have a cell density of at least 9.80E+04 per cm³, at least 9.90E+04 per cm³, at least 1.00E+05 per cm³, or at least 1.05E+05 per cm³. Foaming level, average cell size and cell density can be determined according to methods described in PCT Publication No. WO/2017/166004.

Articles of Manufacture

In an embodiment, the foamable or foamed composition of this disclosure can be applied to a cable, a wire, or a conductor as a sheath or insulation layer in known amounts and by known methods, for example, with the equipment and methods described in U.S. Pat. Nos. 5,246,783, 6,714,707, 6,496,629 and USPA 2006/0045439. Typically, the foamed polyolefin composition can be prepared in a reactor-extruder equipped with a cable-coating die and, after the components of the composition are formulated, the composition is extruded over the cable or conductor as the cable or conductor is drawn through the die. Foaming of the polyolefin composition can be performed at the time of extrusion over the cable or conductor. In such embodiments, extrusion can be performed at a temperature greater than the decomposition temperature of the chemical foaming agent.

Other articles of manufacture that can be prepared from the foamed polymer compositions of this disclosure include fibers, ribbons, sheets, tapes, tubes, pipes, weather-stripping, seals, gaskets, hoses, foams, footwear bellows, bottles, and films. These articles can be manufactured using known equipment and techniques.

Definitions

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

"Wire" means a single strand of conductive metal, e.g., copper or aluminum, or a single strand of optical fiber.

"Cable" means at least one wire or optical fiber within a sheath, e.g., an insulation covering or a protective outer jacket. Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. Typical cable designs are illustrated in U.S. Pat. Nos. 5,246,783, 6,496,629 and 6,714,707.

"Conductor" denotes one or more wire(s) or fiber(s) for conducting heat, light, and/or electricity. The conductor may be a single-wire/fiber or a multi-wire/fiber and may be in strand form or in tubular form. Non-limiting examples of suitable conductors include metals such as silver, gold, copper, carbon, and aluminum. The conductor may also be optical fiber made from either glass or plastic.

"Masterbatch" and like terms denote a concentrated mixture of additives in a carrier resin. In the context of this invention, a masterbatch comprises a concentrated mixture of nucleator in a polyolefin resin. The masterbatch allows for an efficient addition and dispersion of the nucleator to and in the polyolefin. The manufacture and use of masterbatches are well known to those skilled in the art of manufacturing and fabricating plastics and foam articles.

Test Methods

Decomposition Temperature
Determine decomposition temperatures by thermogravimetric analysis (TGA) on TA Instruments® TGA-Q500 thermogravimetric analyzer with a ramp of 10° C./min under $N_2$ from 25 to 800° C.

Weight Loss
Determine weight loss by thermogravimetric analysis (TGA) on TA Instruments® TGA-Q500 thermogravimetric analyzer with a ramp of 10° C./min under $N_2$ from 25 to 800° C.

Liberated Gas Detection
Measure gas yields by the water displacement volume (ml) in a gas burette, connected to the foaming agent (1 gram) heating apparatus.

Proton NMR Spectra
$^1$H NMR spectra are recorded on Bruker® AVANCE III HD (400 MHz) spectrophotometers. Chemical shifts (δ) are determined in ppm from the solvent resonance as the internal standard (DMSO-$D_6$: 2.50 ppm).

Materials

The following materials are employed in the Examples, below.

Cyanuric chloride is commercially available from Adamas-beta, Shanghai, China.

Hydrazine ("$N_2H_4$") is commercially available from Sigma-Aldrich, St. Louis, MO, USA.

Acetonitrile ("MeCN") is commercially available from Sigma-Aldrich, St. Louis, MO, USA.

p-Toluenesulfonyl hydrazide ("TsNHNH$_2$") is commercially available from Sigma-Aldrich, St. Louis, MO, USA.

Triethylamine ("Et$_3$N") is commercially available from Sigma-Aldrich, St. Louis, MO, USA.

Diethyl malonate is commercially available from Sigma-Aldrich, St. Louis, MO, USA.

Sulfuric acid ("$H_2SO_4$") is commercially available from Sigma-Aldrich, St. Louis, MO, USA.

Ethyl acetate is commercially available from Sigma-Aldrich, St. Louis, MO, USA.

Methanol is commercially available from Sigma-Aldrich, St. Louis, MO, USA.

n-Hexane is commercially available from Sigma-Aldrich, St. Louis, MO, USA.

1H-tetrazole-5-carboxylic acid is commercially available from Sigma-Aldrich, St. Louis, MO, USA.

EXAMPLES

Prepare three Comparative Samples (CS1-CS3) and three Samples (S1-S3) according to the following procedures.

CS1 is prepared using the following synthesis route:

(CS1)

Cyanuric chloride (3.68 g, 20.0 mmol) is suspended in H₂O (150 ml) and an 80% solution of N₂H₄ in H₂O (4.0 ml, 103.0 mmol) is added dropwise at 25° C. over a period of 10 minutes. The mixture is stirred at 100° C. overnight. The resulting product (CS1) is then filtered, washed thoroughly with acetonitrile and dried under vacuum. Yield=3.21 g (94%), white powder.

S1 is prepared via a similar synthesis route, but substituting p-toluenesulfonyl hydrazide for hydrazine:

(S1)

Cyanuric chloride (3.68 g, 20.0 mmol) is suspended in acetonitrile (150 ml), p-toluenesulfonyl hydrazide (11.16 g, 60.0 mmol) and triethylamine (404 mg, 4.0 mmol) are added respectively. The mixture is stirred at 90° C. overnight. After completion of the reaction, the mixture is cooled to room temperature, and the resulting suspension was filtered and washed with acetonitrile. Yield=10.61 g (84%), white powder.

S2 and CS2 are prepared according to the following synthesis route, where R is Ts for S2 and H for CS2:

(S2 and CS2)

To a solution of the diethyl malonate (3.20 g, 20.0 mmol) in methanol (150 ml) was added either hydrazine (for CS2) or p-toluenesulfonyl hydrazide (for S2) (40.0 mmol). With robust stirring of the reaction mixture at 0° C., 98% sulfuric acid (0.22 mL, 4.0 mmol) is added dropwise and the mixture is kept at 0° C. After completion of addition, the solution is heated to 70° C. for overnight. Then the solution is cooled to room temperature, and the forming precipitate is filtered to give the crude product. It was allowed to be recrystallized in ethyl acetate/n-hexane to afford the final products S2 and CS2.

S3 and CS3 are prepared according to the following synthesis route, where R is Ts for S3 and H for CS3:

(S3 and CS3)

To a solution of 1H-tetrazole-5-carboxylic acid (2.28 g, 20 mmol) in methanol (150 ml) is added 98% sulfuric acid (0.22 mL, 4.0 mmol) dropwise at 0° C. Then the reaction mixture is heated to 70° C. for 6 hours. Either hydrazine (for CS3) or p-toluenesulfonyl hydrazide (for S3) (20 mmol) is then added in one portion. The reaction mixture is stirred at reflux overnight. Then the solution is cooled to room temperature, and the forming precipitate was filtered to give the crude product. It was allowed to be recrystallized in ethyl acetate/n-hexane to afford the final products S3 and CS3.

Samples S1-S3 and Comparative Samples CS1-CS3 are analyzed using the Test Methods described, above, to determine their decomposition temperature and weight loss. Table 1, below, provides the decomposition performance of S1-S3, CS1-CS3, and, for reference, azodicarbonamide ("ADC").

TABLE 1

| Decomposition Performance of Foaming Agents | | | | | | | |
|---|---|---|---|---|---|---|---|
| Comparative Samples | | | | Inventive Samples | | | |
| Sample No. | Structure | Decomp Temp. (° C.) | Weight Loss (%) | Sample No. | Structure | Decomp Temp. (° C.) | Weight Loss (%) |
| CS1 | (triazine with NHNH₂, H₂NHN, NHNH₂) | 93 | 56 | S1 | (triazine with NHNHTs, TsHNHN, NHNHTs) | 112 | 58 |
| CS2 | (malonyl with H₂NHN, NHNH₂) | 107 | 85 | S2 | (malonyl with TsHNHN, NHNHTs) | 124 | 81 |

TABLE 1-continued

Decomposition Performance of Foaming Agents

| Comparative Samples | | | | Inventive Samples | | | |
|---|---|---|---|---|---|---|---|
| Sample No. | Structure | Decomp Temp. (°C.) | Weight Loss (%) | Sample No. | Structure | Decomp Temp. (°C.) | Weight Loss (%) |
| CS3 |  | 99 | 94 | S3 |  | 156 | 84 |
| ADC |  | 203 | 83 | | | | |

Samples S1-S3 and Comparative Samples CS1-CS3 are analyzed using the Test Methods described, above, to determine the type of gas or gases liberated upon decomposition. Table 2, below, provides the decomposition performance of S1-S3, CS1-CS3, and, for reference, azodicarbonamide.

TABLE 2

Liberated Gases from Foaming Agents

| Comparative Samples | | | Inventive Samples | | |
|---|---|---|---|---|---|
| Sample No. | Structure | Liberated Gas(es) | Sample No. | Structure | Liberated Gas(es) |
| CS1 |  | $N_2$ | S1 |  | $N_2$ |
| CS2 |  | $N_2$, CO | S2 |  | $N_2$, CO |
| CS3 |  | $N_2$, CO | S3 |  | $N_2$, CO |
| ADC |  | $N_2$, CO, $NH_3$, $CO_2$ | | | |

The invention claimed is:

1. A chemical foaming agent comprising one or more of the following compounds shown as structures (III) through (IX):

where Ts is a p-toluenesulfonyl group.

2. A process of foaming a polyolefin, said process comprising:
   (a) combining a polyolefin with a chemical foaming agent to thereby form a foamable polyolefin composition; and
   (b) subjecting the foamable polyolefin composition to a foaming process,
   wherein the chemical foaming agent comprises one or more of the following compounds shown as structures (III) through (IX):

where Ts is a p-toluenesulfonyl group.

3. The process of claim 2, wherein the chemical foaming agent is present in an amount ranging from 0.1 to 1.0 weight percent, based on the total weight of the foamable polyolefin composition, wherein the polyolefin comprises an ethylene-based polymer, wherein the polyolefin is present in an amount ranging from 90 to 99.9 weight percent, based on the total weight of the foamable polyolefin composition.

4. The process of claim 3, wherein the foamable polyolefin composition further comprises an additive selected from the group consisting of antioxidants, cell stabilizers, and combinations thereof.

* * * * *